United States Patent [19]
Peters et al.

[11] Patent Number: 5,169,881
[45] Date of Patent: Dec. 8, 1992

[54] PROCESS FOR TREATING PIGMENTS

[75] Inventors: Kimberly T. Peters, Johnson City; Stephen H. W. Wu, Kingsport, both of Tenn.

[73] Assignee: Eastman Kodak Company, Rochester, N.Y.

[21] Appl. No.: 695,835

[22] Filed: May 6, 1991

Related U.S. Application Data

[62] Division of Ser. No. 426,612, Oct. 24, 1989, Pat. No. 5,055,500.

[51] Int. Cl.$^5$ .............................................. C08J 7/04
[52] U.S. Cl. .................................. 523/319; 523/322; 523/323; 523/326; 524/88; 524/94; 524/107; 524/159; 524/160; 524/190; 524/376; 524/377; 524/386; 524/389; 524/431; 524/539; 524/538

[58] Field of Search .................. 524/88, 94, 107, 159, 524/160, 190, 376, 377, 386, 389, 431, 539, 538; 523/319, 322, 323, 326

[56] References Cited

U.S. PATENT DOCUMENTS 4,847,316 7/1989 Schick et al. .......................... 524/88

Primary Examiner—Melvyn I. Marquis
Assistant Examiner—Frederick Krass
Attorney, Agent, or Firm—Betty J. James; William P. Heath, Jr.

[57] ABSTRACT

The present invention concerns a process for preparing a treated blend which contains pigment material dispersed in a continuous phase of water and a polyester material. The invention also concerns compositions prepared from such process. The polyester material of the treated blend is linear, contains a sulfomonomer, and has an average particle size of less than 1 μm.

12 Claims, 1 Drawing Sheet

PROCESS FOR TREATING PIGMENTS

This is a divisional application of copending application Ser. No. 07/426,612 filed on Oct. 24, 1989, now U.S. Pat. No. 5,055,500.

FIELD OF INVENTION

The present invention is directed to a process for preparing treated blends in which the blends contain pigment materials dispersed in a continuous phase of a water-dissipatable polyester and water.

BACKGROUND OF THE INVENTION

Inorganic pigments such as iron oxides, zinc oxide, talc, titanium oxide, chromium hydroxide, chromium oxide, ferric ammonium ferrocyanide, manganese ammonium pyrophosphate complex (manganese violet), and sodium aluminum sulfosilicates complex (ultramarine blue) are commonly used as cosmetic ingredients. The current methods for pigment dispersion in a cosmetic preparation usually require a series of steps including particle size reduction of a pigment, dispersing the pigment into a liquid base or the total formulation under high shear mixing, and then subjecting the preformulated base or formulation to further homogenization to yield a final product.

Due to the high specific gravity of an inorganic pigment, the pigment tends to settle in a liquid base over a period of time. Furthermore, the pigment materials dispersed in a liquid base may be adversely affected by the liquid vehicle, entrapped air or other ingredients and result in color changes or discoloration. Thus the dispersibility of a pigment material and the color stability of a pigment dispersion may seriously affect the quality of a cosmetic preparation. The ease of processing a pigment is also very desirable in the overall process.

Treatment of pigment surfaces in general is known in the field of coating, cosmetics and ink technology. The art of pigment dispersion is generally taught in a textbook by T. C. Patton, titled "Paint Flow and Pigment Dispersion", 2nd ed. Wiley Interscience, New York, 1978. Specific examples in the prior art where pigment surface treatment is taught can be found in Japanese Patents 86,007,227; 55,007,212; 81,043,264; 86,058,499; 58,096,009; and 81,034,232; and U.S. Pat. Nos. 4,520,153; 4,063,957, and 4,305,853. In addition, U.S. Pat. Nos. 4,704,309 and 4,847,316 teach milling of pigments with an aqueous dispersion of polyester material.

It would be desirable to have a process, and the compositions prepared therefrom, for the preparation of a pigment blend which exhibits good dispersibility in aqueous or selected polar solvent systems and is easy to process.

SUMMARY OF THE INVENTION

In accordance with the present invention, we have discovered a novel process which utilizes a water-dissipatable polymeric material under the influence of moisture and shearing activity to treat the pigment so as to result in a product with desirable properties. When a dispersion made from the treated blend of the present invention is applied to skin, it provides many desirable characteristics such as smooth and uniform feel, film-forming, water-resistivity, ease of removal and non-smudginess. The treated blend optionally can be dried and pulverized to yield a free flowing powder product. When the powder is used in the formulation of eyeshadows and face powders, it provides better adhesion and flow characteristics.

More specifically, the present invention is directed to a process comprising the steps of:

(1) contacting together, in any order, the following:
(A) about 7 to about 48 weight % of a linear, water-dispersible polyester material having an inherent viscosity of at least about 0.1 as measured in a 60/40 parts by weight solution of phenol/tetrachloroethane at 25° C. and at a concentration of 0.5 gram of polyester in 100 ml of solvent, and said polyester material having incorporated therein at least one sulfomonomer,
(B) about 25 to about 73 weight % of a pigment material, and
(C) about 5 to about 50 weight % of water, under sufficient agitation to form a polymer/pigment/water blend, said contacting occurring at a temperature less than or equal to the glass transition temperature (Tg), as measured by differential scanning calorimetry (DSC), of said polyester material, and
wherein
said polymer/pigment/water blend comprises a continuous phase which comprises a major portion of said water and a dispersed phase which comprises a major portion of said pigment material and a major portion of said polyester material, and said polyester material of said polymer/pigment/water blend is in the form of particles having an average particle size of greater than 50 μm;
followed by
(2) subjecting the polymer/pigment/water blend formed by step (1), at a temperature of 5° C. to 80° C., to an amount of shear effective to form a treated pigment blend which comprises a continuous phase which comprises a major portion of said water and a major portion of said polyester material and a dispersed phase which comprises a major portion of said pigment material, and wherein said polyester material of said treated blend has an average particle size of less than 1 μm; and wherein said treated pigment blend has a zero shear rate viscosity of greater than or equal to 500,000 poise.

The process of the invention also includes a pigment composition comprising
(A) about 7 to about 48 weight % of a linear, water-dispersible polyester material having an inherent viscosity of at least about 0.1 as measured in a 60/40 parts by weight solution of phenol/tetrachloroethane at 25° C. and at a concentration of 0.5 gram of polyester in 100 ml of solvent, and said polyester material having incorporated therein at least one sulfomonomer,
(B) about 25 to about 73 weight % of a pigment material, and
(C) about 5 to about 50 weight % of water, wherein said pigment composition comprises a continuous phase which comprises a major portion of said water and a major portion of said polyester material and a dispersed phase which comprises a major portion of said pigment material, and wherein said polyester material of said pigment composition has an average particle size of less than 1 μm; and wherein said pigment composition has a zero shear rate viscosity of greater than or equal to 500,000 poise.

The present invention also is related to dispersions prepared from the treated blends of this invention in which said treated pigment blend (or pigment composition of the invention) is dispersed in a polar solvent system which preferably comprises at least 10 weight % water.

DETAILED DESCRIPTION OF THE INVENTION

Figure 1:
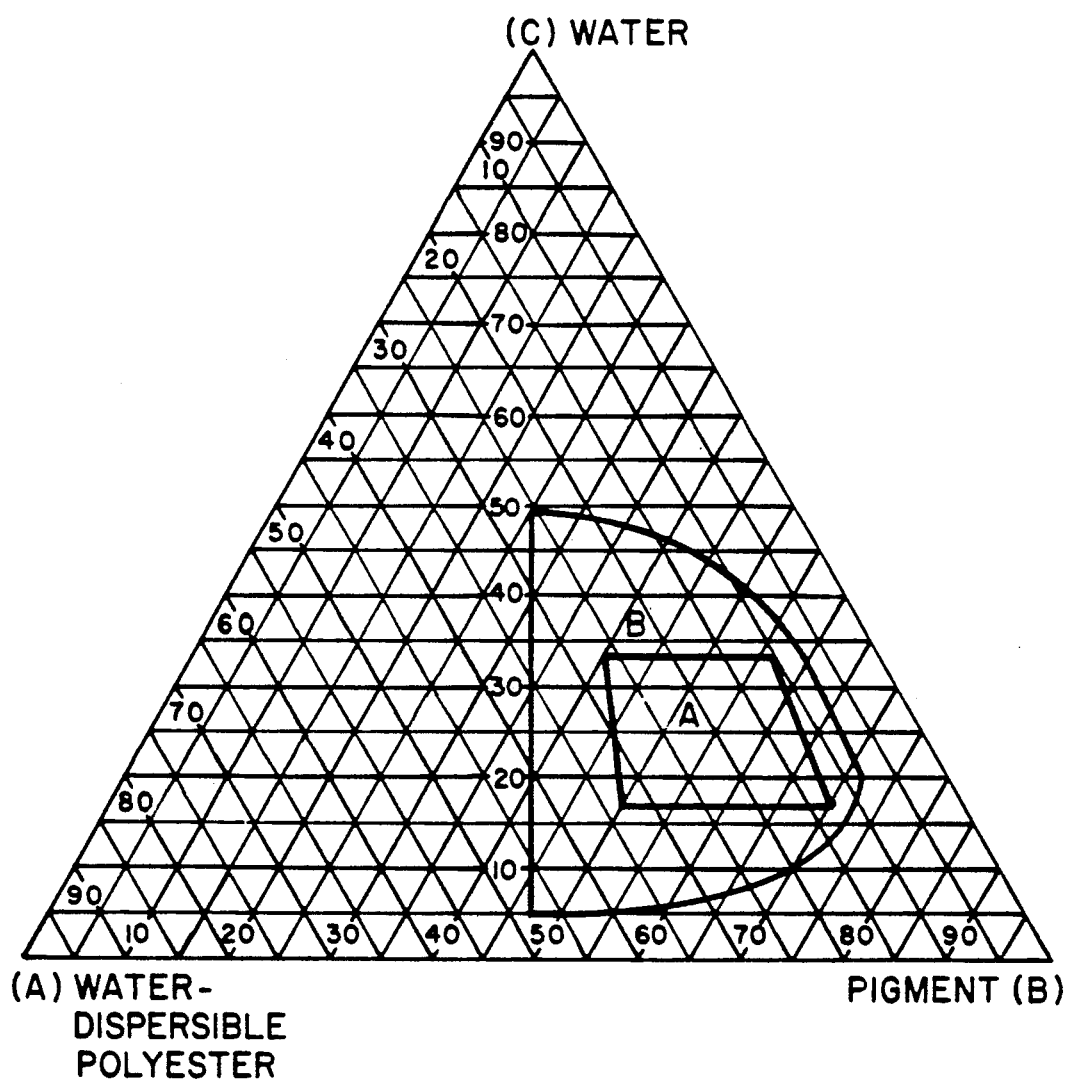
FIG. 1 is a tri-component graph depicting preferred and most preferred weight percentages of the three components of the process and composition of the invention. Zone B depicts a broader range and Zone A depicts the most preferred range.

The term "pigment" as used in this invention may be defined as any natural or synthetic inorganic or organic substance that imparts a color including black or white to other materials. The pigment materials treated by the process of the present invention (i.e., treated pigment blends or pigment compositions of the invention), optionally with water removed followed by optional breaking, preferably exhibit one or more of the following desirable properties:
a. dispersible in aqueous or polar solvent systems—the material can be dispersed in aqueous or polar solvent to form a fine uniform dispersion;
b. film-forming—when an aqueous dispersion of the treated blend is applied to skin, it has a smooth feel and results in a flexible, smudge-proof, and water-resistant film;
c. non-dustiness—the treated blend is preferably in the form of a non-dusty granular product;
d. after an optional water removal step, the product is suitable for grinding for particle size reduction—the resulting product is a compressible free-flowing powder; and
e. ease for direct incorporation into mascara formulation and cosmetic base.

In the process and composition of the present invention component (A) is preferably about 10 to about 33 weight %, component (B) is preferably about 40 to about 71 weight %, and component (C) is preferably about 16 to about 34 weight %. It is also preferred that the amount of water contacted with said polyester material in steps (1) and (2) is sufficient to lower the Tg of the polymer by at least 20° C. A preferred range of components is shown in FIG. 1 as Zone B and the most preferred range of components is shown in FIG. 1 as Zone A.

In the process of the present invention the temperature in step (2) can vary depending upon the particular polyester material employed as well as other conditions. For example, a generally preferred temperature for step (2) is about 5° to 75° C., a more preferred general range is about 25°-75° C. and a most preferred general range is about 30° to 60° C. However, for a given polymer, a most preferred range may be 25° to 60° C., 25° to 50° C., 25° to 35° C. or 35° to 45° C.

The shear applied in step (2) can be effected by any means commonly known in the art such as extrusion, ball milling, roll milling, high shear mixing, and the like.

The effective amount of shear in step (2) of the process of the present invention is typically substantially the same as that generated in a twin screw extruder operated at 5 to 70 revolutions per minute (rpm) through a perforated screen or die plate with perforations of 1.5 to 3.5 millimeters (mm) in diameter. The twin screw extruder is preferably a Luwa EXDS-60 extruder. Preferred speed is 30 to 50 rpm.

Shear may also be applied with a Haake Buchler Rheomix type mixer equipped with roller mixing blades. The mixing chamber contains two intersecting cylinders in which the left blade turns three revolutions for each two revolutions of the right blade causing the material to follow a side to side figure eight mixing path. The capacity of the mixer is 70 cc or approximately 45 to 65 grams and is operated at 10 to 40 rpm for 1 to 10 minutes at 25°-35° C. The torque associated with this mixing is 500 to 1500 meter.grams.

The temperature and shear in step (2) of the process of the invention is preferably sufficient to liquefy the polyester material. After step (1), the polymer/pigment/water blend has a continuous phase and a dispersed phase. The continuous phase of the polymer/pigment/water blend preferably comprises substantially all the water and the dispersed phase comprises substantially all the polyester material and substantially all the pigment material. After performing step (2) wherein the polyester is liquefied, the treated pigment blend comprises a continuous phase which preferably comprises substantially all the water and substantially all the polyester material and a dispersed phase which comprises substantially all the pigment material.

In step (1) the polyester material is in the form of particles having an average size of greater than 50 micrometers ($\mu$m), preferably greater than 100 $\mu$m. After step (2) is performed, the average size of the polyester material is less than 1 $\mu$m, preferably less than 0.5 $\mu$m, and more preferably less than 0.1 $\mu$m.

The amount and type of agitation in step (1) is preferably simple mixing sufficient to form a substantially intermixed blend having the required characteristics. The temperature for step (1) must be at or below the Tg as measured by DSC of the dry polyester material; typically such temperature is about 20° C. to about 45° C., more typically about 25° C. to about 35° C. The pigment material, polyester material, and water can be added in any order. The polyester material must be in the form of particles having an average particle size of at least 50 $\mu$m when the polyester material is contacted with pigment material. This means that the polyester material cannot be contacted or dispersed with water and then contacted with the pigment material as disclosed in U.S. Pat. Nos. 4,704,309 and 4,847,316, since the typical particle size of polyester material dispersed in water is about 20 to 25 nanometers (nm). Following the teachings of the prior art results in a product of much lower viscosity than required by the present invention which is not suitable for forming and drying.

After performing step (2), the treated pigment blend of the invention is a semisolid malleable material having a zero shear rate viscosity of at least 500,000 poise, preferably at least 1,000,000 poise. Typical treated pigment blends have a zero shear rate viscosity of 1,000,000 to 10,000,000 poise or higher. Zero order shear rate can be determined by use of a Rheometrics Stress Rheometer, Model 8600 at 24° C. with a constant shear stress of 2000 dynes/cm$^2$. The highest viscosity of a finished ink mentioned in U.S. Pat. No. 4,847,316 is 60 seconds as measured with a #2 Zahn cup according to ASTM D-4212-82. This is roughly equivalent to 1.5 poise.

The particle size of the pigment material after step (2) remains the same as in step (1); only the degree of dispersion is higher resulting in reduced agglomeration.

The process of the present invention includes the optional step of removing water from the treated pigment blend formed by step (2). The amount of water removed is preferably sufficient to form a substantially solid material. The substantially solid material usually has a moisture content of less than 20 weight %, preferably less than 10 weight %, more preferably less than 5 weight %, and most preferably less than 1 weight %. The water can be removed by standard techniques known in the art, for example, pressing, hot-air drying, and the like.

After a substantially solid material is formed by water removal, a substantially non-dusty particulate material can optionally be formed by simple breaking techniques such as grinding.

Any of the treated pigment blend, substantially solid material, or substantially non-dusty particulate material of the present invention can be used in cosmetic applications directly or can be dispersed in a polar solvent system and then used in cosmetic applications. Such dispersal in a polar solvent system can be accomplished by techniques well known in the art and/or by those techniques disclosed herein. The polar solvent system is preferably aqueous and preferably comprises at least about 10 weight % water, more preferably at least about 50 weight % water.

The present invention also contemplates cosmetic formulations employing the pigment compositions (whether or not dried and/or ground) of the invention. Such a formulation comprises (I) about 10 to about 60 weight % of an oil phase, and (II) about 40 to about 90 weight % of a water phase which comprises a pigment composition comprising:

(A) about 7 to about 48 weight % of a linear, water-dispersible polyester material having an inherent viscosity of at least about 0.1 as measured in a 60/40 parts by weight solution of phenol/tetrachloroethane at 25° C. and at a concentration of 0.5 gram of polyester in 100 ml of solvent, and said polyester material having incorporated therein at least one sulfomonomer, (B) about 25 to about 73 weight % of a pigment material, and (C) about 5 to about 50 weight % of water, wherein said pigment composition comprises a continuous phase which comprises a major portion of said water and a major portion of said polyester material and a dispersed phase which comprises a major portion of said pigment material, and wherein said polyester material of said pigment composition has an average particle size of less than 1 μm; and wherein said pigment composition has a zero shear rate viscosity of greater than or equal to 500,000 poise;

wherein about 1 to about 30 weight % of the formulation is said pigment composition, and wherein about 1 to about 25 weight percent of the formulation is at least one emulsifier which can be in the oil phase, the water phase or both.

It is preferred that component (I) of the cosmetic formulation is present in an amount of about 20 to about 30 weight % and that component (II) is present in an amount of about 80 to about 70 weight percent. It is also preferred that about 15 to about 25 weight percent of the formulation is said pigment composition and that about 10 to about 20 weight % of the formulation is said emulsifier.

The oil phase of the cosmetic formulation preferably comprises one or more of the following: fatty acids, waxes, liquid hydrocarbons, vegetable oils, fatty acid esters, cetyl alcohol, stearyl alcohol, ethoxylated cetyl-stearyl alcohols, propylene glycol, glyceryl esters, sorbitan, ethoxylated sorbitan esters and their derivatives, lanolin and its derivatives, antioxidants, preservatives, and perfume.

In addition to said pigment composition, the water phase of the cosmetic formulation preferably comprises one or more of the following: water, lecithin and its derivatives, surfactants, gums, clays, polymers, polyols, preservatives, and alkalies.

The cosmetic formulation of the present invention is typically a mascara or a liquid make-up, a cosmetic base, or the like. The pigment composition of the invention can also be incorporated into other cosmetic compositions such as eyeshadows, face powders, or the like. It is also contemplated that the pigment composition of the invention can be incorporated into other formulations such as paints or inks.

Polyester Polymers

The liquefiable polyesters useful in the present invention are described in U.S. Pat. Nos. 3,546,008; 4,340,519; 3,734,874; 3,779,993; and 4,233,196, incorporated herein by reference in their entirety. The polyesters preferably contain at least one ether-containing glycol component such as diethylene glycol or a polyethylene glycol. The polyester material is preferably ground or pulverized to a mesh size of about 20 to about 200 mesh prior to performing step (1) of the invention.

The polyester material useful in the present invention is preferably one or more linear water-dissipatable polymers having carbonyloxy linking groups in the linear molecular structure wherein up to 80% of the linking groups are carbonylamido linking groups, the polymer having an inherent viscosity of from about 0.1 to about 1.0 measured in a 60/40 parts by weight solution of phenol/tetrachloroethane at 25° C. and at a concentration of 0.5 gram of polymer in 100 mL of the solvent, the polymer containing substantially equimolar proportions of acid equivalents (100 mole %) to hydroxy and amino equivalents (100 mole %), the polymer comprising the reaction products of reactants selected from (1), (2), (3), and (4), or the ester forming or esteramide forming derivatives thereof, as follows, wherein all stated mole percentages are based on the total of all acid, hydroxyl and amino equivalents being equal to 200 mole %:

(1) at least one difunctional dicarboxylic acid;
(2) from about 4 to about 25 mole % of at least one difunctional sulfomonomer containing at least one metallic sulfonate group or nitrogen-contained non-metallic sulfonate group attached to an aromatic or cycloaliphatic nucleus wherein the functional groups are hydroxy, carboxyl or amino;
(3) at least one difunctional reactant selected from a glycol or a mixture of a glycol and diamine having two —NRH groups, the glycol containing two —CH₂—OH groups of which (a) at least 15 mole % is a poly(ethylene glycol) having the structural formula

n being an integer of from 2 to about 20, or (b) of which from about 0.1 to less than about 15 mole % is a poly(ethylene glycol) having the structural formula

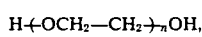

n being an integer of between 2 and about 500, and with the proviso that the mole % of said poly(ethylene glycol) within said range is inversely proportional to the quantity of n within said range;

(4) from none to about 40 mole % of difunctional reactant selected from hydroxycarboxylic acids having one —C(R)$_2$—OH group, aminocarboxylic acids having one —NRH group, and amino-alcohols having one —C(R)$_2$—OH group and one —NRH group, or mixtures of said difunctional reactants; and wherein each R in the (3) and (4) reactants is a hydrogen atom or an alkyl group of 1 to 4 carbons. The polyester typically has an inherent viscosity of at least 0.1 and preferably at least 0.3 and a glass transition temperature ranging from 25° to 90° C. when the polymers are in the dry state. When the polymers contain 1-25% water of its own weight, the glass transition temperatures may drop to a lower range usually below 50° C. A preferred embodiment is where said polyester has an inherent viscosity of from about 0.28 to about 0.35, a Tg of about 50 to 60, an acid moiety of from about 75 to about 84 mole % isophthalic acid and conversely from about 25 to about 16 mole % 5-sodiosulfoisophthalic acid, and a glycol moiety of from about 45 to about 60 mole % diethylene glycol and conversely from about 55 to about 44 mole % 1,4-cyclohexanedimethanol or ethylene glycol or mixtures thereof. More preferred is wherein said acid moiety comprises from about 80 to about 83 mole % isophthalic acid and conversely from about 20 to about 17 mole % 5-sodiosulfoisophthalic acid, and said glycol moiety comprises from about 52 to about 56 mole % diethylene glycol and conversely from about 48 to about 44 mole % 1,4-cyclohexanedimethanol.

In another preferred embodiment said polyester material has an inherent viscosity of about 0.38 to 0.44, a Tg of about 27 to 31, an acid moiety of about 87 to 91 mole % isophthalic acid and conversely about 13 to 9 mole % 5-sodiosulfoisophthalic acid, and a glycol moiety of about 98 to 100 mole % diethylene glycol.

In still another preferred embodiment said polyester material has an inherent viscosity of about 0.34 to 0.38, a Tg of about 36 to 38, an acid moiety of about 87 to 91 mole % isophthalic acid and conversely about 13 to 9 mole % 5-sodiosulfoisophthalic acid, and a glycol moiety of about 76 to 80 mole % diethylene glycol and conversely about 20 to about 24 mole % 1,4-cyclohexanedimethanol.

Typical compositions are given as follows:

| Polyester Designation | IPA mole % | SIP mole % | DEG mole % | CHDM mole % | IV | $T_g$ |
|---|---|---|---|---|---|---|
| AQ29 | 89 | 11 | 100 | 0 | 0.42 | 29 |
| AQ38 | 89 | 11 | 78 | 22 | 0.36 | 38 |
| AQ55 | 82 | 18 | 54 | 46 | 0.33 | 55 |

Where IPA = isophthalic acid, SIP = 5-sodiosulfoisophthalic acid, DEG = diethylene glycol, CHDM = 1,4-cyclohexanedimethanol.

The inherent viscosities (IV) of the particular polyester materials useful herein are at least about 0.1 and preferably range from about 0.1 to about 1.0 determined according to ASTM D2857-70 procedure, in a Wagner Viscometer of Lab Glass, Inc., of Vineland, N.J., having a ½ ml. capillary bulb, using a polymer concentration about 0.5% by weight in 60/40 by weight of phenol/tetrachloroethane. The procedure is carried out by heating the polymer/solvent system at 120° C. for 15 minutes, cooling the solution to 25° C. and measuring the time of flow at 25° C. The IV is calculated from the equation $$(\eta) = \frac{\ln \frac{t_s}{t_o}}{C}$$

where:

$(\eta)$ = inherent viscosity at 25° C. at a polymer concentration of 0.25 g/100 ml. of solvent;

ln = natural logarithm;

$t_s$ = sample flow time;

$t_o$ = solvent-blank flow time; and

C = concentration of polymer in grams per 100 ml. of solvent = 0.25.

The units of the inherent viscosity throughout this application are in deciliters/gram.

Pigment Materials

The pigment materials useful in this process include water-insoluble, or sparingly water-soluble inorganic and organic pigments, pearlants and Lakes commonly used in cosmetics, paints, coatings, and inks. A Lake is a pigment formed by precipitation and absorption of an organic dye on an insoluble base or substrate, commonly alumina, barium, or calcium hydrates. It is noted that pigments having large amounts of bivalent or multivalent ionizable cations are not preferred since they interfere with the water dispersibility of the polyester material. Therefore, Lake pigments containing such cations are not preferred.

Typical inorganic pigments include iron oxides of various colors (yellow, red, brown and black), ferric ammonium ferrocyanide (blue), manganese violet, ultramarine blue, chrome oxide (green), talc, lecithin modified talc, zeolite, kaolin, lecithin modified kaolin, titanium dioxide (white) and mixtures of said inorganic pigments. Typical pearlants include mica, bismuth oxychloride and treated mica such as titanated micas, lecithin modified mica. Typical Lakes useful in this invention are primary FD&C Lakes and their blends.

Organic pigments useful in this invention include natural colorants and synthetic monomeric and polymeric colorants. Typical examples are phthalocyanine blue and green pigments, diarylide yellow and orange pigments, and azo-type red and yellow pigments such as toluidine red, litho red, naphthol red and brown pigments.

Generally copolymer pigments useful in this invention are water insoluble polymers such as nylon powder, polyethylene and polyester colorants. The types of polyesters employed in this invention may include linear, thermoplastic, crystalline or amorphous materials produced using one or more diols and one or more dicarboxylic acids copolymerized with colorants. In general, the diol components of the polyester include examples such as neopentyl glycol, ethylene glycol, 1,4-cyclohexanedimethanol, 1,2-propanediol, 1,3-propanediol, 1,6-hexanediol, 1,2-cyclohexanediol, 1,4-cyclohexanediol, 1,10-decanediol, 1,2-cyclohexanedimethanol, 1,3-cyclohexanedimethanol, X,8-bis(hydroxymethyl) tricyclo-[5.2.1.0]-decane, wherein X represents 3, 4, or 5; and diols containing one or more oxygen atoms in the chain, e.g., diethylene glycol, triethylene glycol, dipropylene glycol, or tripropylene glycol and the like. These diols contain 2 to 18, preferably 2 to 12 carbon atoms. In addition, cycloaliphatic diols can be used in their cis and trans configuration or as a mixture of both forms. The acid components (aliphatic, alicyclic, or aromatic dicarboxylic acids) of the polyester may consist of terephthalic acid, naphthalene-2,6-dicarboxylic acid, isophthalic acid, 1,4-cyclohexanedicarboxylic acid, 1,3-cyclohexanedicarboxylic acid, succinic acid and the like. The anhydride and esters of the dicarboxylic acids can likewise be employed.

The colorants copolymerized with polyesters include 2,2'-(9,10-dihydro-9,10-dioxo-1,5-anthracenediyl)-diimino) bis-benzoic acid, methyl 3-[4-[[2-(acetyloxy) ethyl] ethylamino]-2-methylphenyl]-2-cyano-2-propenoate, 1,5-bis[(3-hydroxy-2,2-dimethylpropyl)-amino] anthraquinone and other dyes containing two reactive primary alcohol, acid, ester or acetyloxy groups. The colorant content in the polymer is in the range of 8 to 50%.

Exemplary useful C.I. pigments for use in the present invention are given in the following table:

| Pigments | |
|---|---|
| Generic Name | C.A. Index/Chemical Name |
| C.I. Pigment Yellow 17 | Butanamide, 2,2'-[(3,3'-dichloro[1,1'-biphenyl] 4,4'-diyl)bis(azo)bis [N-(2-methoxyphenyl)-3-oxo- |
| C.I. Pigment Blue 27 | Ferrate (4-1), hexakis (cyano-C)-ammonium iron (3+)(1:1:1) |
| C.I. Pigment Red 49:2 | 1-Naphthalenesulfonic acid, 2-[(2-hydroxy-1-naphthalenyl)azo]-, calcium salt (2:1) |
| C.I. Pigment Red 81:1 | Benzoic acid, 2,-[6-ethyl-amino)-3-(ethylimino)-2,7-dimethyl-3H-xanthen-9-yl]-, ethyl ester, w/molybdenum tungsten hydroxide oxide phosphate |
| C.I. Pigment Red 81:3 | Benzoic acid, 2-[6-ethyl-amino)-3-ethylimino)-2,7-dimethyl-3H-xanthen-9-yl]-, ethyl ester, molybdate-silicate |
| C.I. Pigment Red 81:x | Benzoic acid, 2-[6-(ethyl-amino)-3-(ethylimino)-2,7-dimethyl-3H-xanthen-9-yl]-, ethyl ester, molybdate-phosphate |
| C.I. Pigment Yellow 83 | Butanamide, 2,2'-[(3,3'-dichloro[1,1'-biphenyl]-4,4'-diyl)bis(azo)bis[N-(4-chloro-2,5-dimethoxy-phenyl)-3-oxo- |
| C.I. Pigment Red 57:1 | 2-Naphthalenecarboxylic acid, 3-hydroxy-4-[(4 methyl-2-sulfophenyl)azo]-, calcium salt (1:1) |
| C.I. Pigment Red 49:1 | 1-Naphthalenesulfonic acid, 2-[(2-hydroxy-1-naphthalenyl)azo]-, barium salt (2:1) |
| C.I. Pigment Violet 23 | Diindolo[3,3',2'm] triphenodioxazine, 8,18-dichloro-5,15-diethyl-5,15-dihydro- |
| C.I. Pigment Green 7 | C.I. Pigment Green 7 |
| C.I. Pigment Blue 61 | Benzenesulfonic acid, [[4-[[4-phenylamino)-phenyl]-[4-(phenylimino)-2,5-cyclohexadien-1-ylidene]methyl]-phenyl] amino]- |
| C.I. Pigment Red 48:1 | 2-Naphthalenecarboxylic acid, 4-[(5-chloro-4-methyl-2-sulfophenyl)azo]-3-hydroxy-, barium salt (1:1) |
| C.I. Pigment Red 52:1 | 2-Naphthalenecarboxylic acid, 4-[(4-chloro-5-methyl-2-sulfophenyl)azo]-3-hydroxy-, calcium salt (1:1) |
| C.I. Pigment Violet 1 | Ethanaminium, N-[9-(2-carboxyphenyl)-6-(diethyl-amino)-3H-xanthen-3-ylidene]-N-ethyl-, molybdatetungstate-phosphate |
| C.I. Pigment White 6 | Titanium oxide (TiO$_2$) |
| C.I. Pigment Blue 15 | Copper, [29H, 31H-phthalocyaninato (2-)-N$^{29}$, N$^{30}$, N$^{31}$, N$^{32}$]-, (Sp-4-1) |
| C.I. Pigment Yellow 12 | Butanamide, 2,2'-[(3,3'-dichloro[1,1'-biphenyl]-4,4'-diyl)bis(azo)]bis[3-oxo-N-phenyl- |
| C.I. Pigment Blue 56 | Benzenesulfonic acid, 2-methyl-4-[[4-[(3-methylphenyl)amino] phenyl]-[4-[(3-methyl-phenyl)-imino]-2-5-cyclohexadien-1-ylidene]methyl]-phenyl] amino]- |
| C.I. Pigment Orange 5 | 2-Naphthalenol, 1-[(2,4-dinitrophenyl)azo]- |
| C.I. Pigment Black 7 | Carbon black |
| C.I. Pigment Yellow 14 | Butanamide, 2,2'-[(3,3'-dichloro[1,1'-biphenyl]-4,4'-diyl)bis(azo)]bis-[N-(2-methylphenyl)-3-oxo- |
| C.I. Pigment Red 48:2 | 2-Naphthalenecarboxylic acid, 4-[(5-chloro-4-methyl-2-sulfophenyl) azo]-3-hydroxy-, calcium salt (1:1) |
| C.I. Pigment Blue 15:3 | Copper, [29H, 31H-phthalocyaninato (2-)-N$^{29}$, N$^{30}$, N$^{31}$, N$^{32}$]-, (SP-4-1)- |
| C.I. Pigment Yellow 1 | Butanamide, 2-[(4-methyl-2-nitrophenyl)azo]-3-oxo-N-phenyl- |
| C.I. Pigment Yellow 3 | Butanamide, 2-[(4-chloro-2-nitrophenyl) azo]-N-(2-chlorophenyl) -3-oxo- |
| C.I.Pigment Yellow 13 | Butanamide, 2,2'-[(3,3'-dichloro[1,1'-biphenyl]-4,4'-diyl)bis(azo)]bis [N-(2,4-dimethylphenyl)-B-oxo- |
| C.I. Pigment Orange 16 | Butanamide, 2,2'-[(3,3' dimethoxy[1,1'-biphenyl]-4,4'-diyl)bis(azo)]bis [3-oxo-N-phenyl- |
| C.I. Pigment Yellow 55 | Butanamide, 2,2'-[(3,3'-dichloro[1,1'-biphenyl] -4,4'-diyl)bis(azo)]bis [N-(4-methylphenyl)-3-oxo- |
| C.I. Pigment Red 41 | 3H-Pyrazol-3-one,4,4'-[(3,3'-dimethoxy[1,1'-biphenyl]4,4'-diyl)bis (azo)]bis[2,4-dihydro-5-methyl-2-phenyl- |
| C.I. Pigment Orange 34 | 3H-Pyrazol-3-one,4,4'-[(3,3'-dichloro[1,1'-biphenyl]-4,4'-diyl)bis (azo)]bis[2,4-dihydro-5-methyl-2-(4-methylphenyl)- |
| C.I. Pigment Blue 62 | 4,4'-Bis(diethylamino) |

Pigments

| Generic Name | C.A. Index/Chemical Name |
|---|---|
| | benzophenone condensed with N-ethyl-1-naphthylamine in toluene with phosphorous oxychloride and converted to the copper ferrocyanide salt (PTMA salt in P.Blue 1) |
| C.I. Pigment Violet 1 | Ethanaminium, N-[9-(2-carboxyphenyl)-6-(diethylamino)-3H-xanthen-3-ylidene]-N-ethyl-, molybdatetungstatephosphate |
| C.I. Pigment Red 22 | 2-Naphthalenecarboxamide, 3-hydroxy-4-[(2-methyl-5-nitrophenyl)azo]-N-phenyl- |
| C.I. Pigment Red 170 | 2-Naphthalenecarboxamide, 4-[[(4-(aminocarbonyl)phenyl]azo]-N-(2-ethoxyphenyl)-3-hydroxy- |
| C.I. Pigment Red 88 | Benzo[b]thiophen-3(2H)-one, 4,7-dichloro-2-(4,7-dichloro-3-oxobenzo[b]-thien-2(3H)-ylidene)- |
| C.I. Pigment Yellow 151 | A diazotized aniline derivative coupled with an acetoacetyl derivative of 5-aminobenzimidazolone |
| C.I. Pigment Violet 23 | Diindolo[3,3',2'm]triphenodioxazine, 8-18-dichloro-5,15-diethyl-5,15-dihydro- |
| C.I. Pigment Red 184 | A diazotized substituted aniline coupled with a derivative of 3-hydroxy-2-naphthanilide |
| C.I. Pigment Blue 1:2 | Ethanaminium, N-[4-[[4-(diethylamino)phenyl][4-(ethylamino)-1-1 naphthalenyl]methylene]-2,5-cyclohexadien-1-ylidene]-N-ethyl-, [orthosilicato(4-)] hexatriacontaoxo-dodecamolybdate(4)-(4:1) |
| C.I. Pigment Red 3 | 2-Naphthalenol, 1-[(4-methyl-2-nitrophenyl)azo]- |
| C.I. Pigment Blue 15:1 | Copper,[29H,32H-phthalocyaninato(2-)-N$^{29}$,N$^{30}$,N$^{31}$, N$^{32}$]-,(SP-4-1)- or Copper,[chloro-29H,31H-phthalocaninato (2-1)-N$^{29}$,N$^{30}$,N$^{31}$, N$^{32}$]- |
| C.I. Pigment Red 23 | 2-Naphthalenecarboxamide, 3-hydroxy-4-[(2-methoxy-5-nitrophenyl)azo]-N-(3-nitrophenyl)- |
| C.I. Pigment Red 112 | 2-Naphthalenecarboxamide, 3-hydroxy-N-(2-methylphenyl)-4-[(2,4,5-trichlorophenyl)azo]- |
| C.I. Pigment Yellow 126 | A tetrazotized derivative of 3,3-dichlorobenzidene coupled with a derivative of acetoacetanilide |
| C.I. Pigment Red 169 | 3-Ethylamino-p-cresol condensed with phthalic anhydride, esterified with ethanol and a mineral acid, and converted to the copper ferrocyanide complex (chloride salt is C.I. Basic Red 1, PTMA salt is P.Red 81:1). |
| C.I. Pigment Orange 5 | 2-Naphthalenol, 1-[(2,4-dinitrophenyl)azo]- |
| C.I. Pigment Orange 13 | 3H-Pyrazol-3-one, 4,4'-[(3,3'-dichloro[1,1'-biphenyl]-4,4'-diyl)bis(azo)]bis[2,4-dihydro-5-methyl-2-phenyl- |
| C.I. Pigment Orange 34 | 3H-Pyrazol-3-one, 4,4'-[(3,3'-dichloro[1,1'-biphenyl]-4,4'-diyl)bis(azo)]bis[2,4-dihydro-5-methyl-2-(4-methylphenyl)- |
| C.I. Pigment Red 10 | 2-Naphthalenecarboxamide, 4-[(2,5-dichlorophenyl)azo]-3-hydroxy-N-(4-methylphenyl)- |
| C.I. Pigment Blue 1:X | Ethanaminium, N-[4-[[4-(diethylamino)phenyl][4-(ethylamino)-1-naphthalenyl]methylene]-2,5-cyclohexadien-1-ylidene]-N-ethyl-, molybdatephosphate |
| C.I. Pigment Yellow 42 | Iron oxide ($Fe_2O_3$) hydrate |
| C.I. Pigment Red 101 | Iron oxide ($Fe_2O_3$) |
| C.I. Pigment Brown 6 | Iron oxide ($Fe_2O_3$), some FeO and $Fe_2O_3.H_2O$ |
| C.I. Pigment Brown 7 | Iron oxide ($Fe_2O_3$) plus varying amounts of clay |
| C.I. Pigment Brown 7:X | $Fe_2O_3$. × $MnO_2$ with varying amounts of clay |
| C.I. Pigment Black 11 | $FeO.Fe_2O_3$ |
| C.I. Pigment Metal 1 | Aluminum |
| C.I. Pigment Metal 2 | Copper, zinc |

The following examples are to illustrate the invention but should not be construed as a limitation thereon. The polyester designations "AQ55", "AQ38", and "AQ29" are as described hereinbefore. All percentages are by weight unless indicated otherwise.

EXAMPLE 1

This example illustrates the effect of moisture on the glass transition temperature of AQ55.

| Moisture in AQ55 % Polymer Weight | Tg*, °C. |
|---|---|
| 0.0 | 55.0 |
| 1.0 | 49.0 |
| 2.0 | 43.0 |
| 3.0 | 40.0 |
| 5.0 | 35.0 |
| 5.8 | 31.0 |
| 12.0 | 20.0 |
| 23.5 | 14.0 |

*measured by DSC

EXAMPLE 2

This example illustrates the lowering of the glass transition temperature (Tg) of AQ38 in an 80:20 pigment/polymer blend with the addition of 34% of the dry weight of water.

The Tg of the sample is determined by differential scanning calorimetry. Scans are made between −30° and 150° C. The results are listed below:

| Sample Description | Tg, °C. |
|---|---|
| Pulverized AQ38 | 37.0 |
| Dry pigment/polymer blend | 37.1 |
| Polymer/pigment/water blend before | None detected |

| Sample Description | Tg, °C. |
|---|---|
| processing (after step (1) of the invention) | (< −30) |
| Treated pigment blend after processing (after step (2) of the invention) | None detected (< −30) |
| Dried, processed substantially solid material | 37.4 |

EXAMPLE 3

This example illustrates the preparation of a solid, non-dusty, granular pigment blend material by employing the process of this invention.

| Ingredients | Amount (g) | (%) |
|---|---|---|
| Iron Oxide (black) | 2400 | 57.1 |
| AQ38 | 600 | 14.3 |
| Water | 1200 | 28.6 |

(1) The AQ38 is pulverized to a powder with an average particle size of 60 to 80 mesh.
(2) The polymer powder is blended with the iron oxide pigment using a suitable mixer such as a Ross double planetary mixer, Sigma blade mixer or Hobart mixer.
(3) Water is added while mixing to form a moist blend.
(4) The blend is extruded to form cylindrical extrudates such as by radial extrusion on a Luwa extruder. The temperature of the extrudate does not exceed 30° C.
(5) The extrudate is rounded to form a granular pigment blend such as by using a Luwa Marumarizer.
(6) The granules are tray dried at 55° C. for up to 8 hours to remove the water and yield a non-dusty, granular pigment material.

EXAMPLE 4

This example illustrates the preparation of an aqueous pigment dispersion using material obtained from Example 3.

Forty-five g of material from Example 3 is added to 45 g of water and stirred for 5 minutes with a laboratory stirrer equipped with a paddle blade. The mixture is then heated to 65° C. while stirring. The dispersion is removed from heat and stirring continued until the dispersion reaches room temperature. The result is a fine uniform dispersion of low viscosity. When applied to the skin, the dispersion has a very smooth and creamy feel. When allowed to dry on the skin it forms a continuous flexible film of good color depth. The film is not removed even when held under running water for several minutes and shows no signs of color bleeding or smudging even with gentle rubbing.

Fineness of dispersion is measured with a grind gage. Measurements are made to the nearest micron at the first point at which four scratches are observed. The particle size of the dispersion prepared above is measured by grind gage to be 4 microns.

A comparison is made to an aqueous dispersion of untreated iron oxide in water prepared in the same manner as described above. The result is a viscous dispersion and the average of three measurements on a grind gage is 31 microns.

EXAMPLE 5

This example illustrates the need for subjecting the polymer/pigment/water blend to shearing activity.

A pigment/polymer blend is prepared by mixing 160 g of black iron oxide and 40 g of pulverized AQ38 using an egg beater type mixer. Sixty g of water is added to the blend while mixing is continued to form a damp, granular blend. The blend is heated over a steam bath and stirred gently with a spatula. The remainder of the water is removed by tray drying. The resulting material is a non-dusty granular powder.

The material is dispersed in water as described in Example 4 and the particle size of the dispersion measured with a grind gage. The average of three measurements on a grind gage is 36 microns. When the dispersion is applied to the skin it has a gritty feel and forms a discontinuous film upon drying.

EXAMPLE 6

This example further illustrates the necessity of subjecting the polymer/pigment/water blend to shearing activity.

An aqueous dispersion of iron oxide and AQ38 is prepared by adding a homogeneous blend of 15 g of AQ38 and 60 g of black iron oxide to 75 g of water while stirring. The dispersion is then heated to 85° C. and this temperature maintained for one hour while stirring is continued. The dispersion is then allowed to cool to room temperature and the fineness of dispersion measured with a grind gage. The average of three measurements is 20 microns.

EXAMPLE 7

This example illustrates the necessity of adding water to lower the Tg of the polymer and provide lubrication necessary for processing.

Several dry blends of black iron oxide and AQ38 powder were prepared at the following ratios: 50:50, 60:40 and 75:25. An attempt was made to extrude each blend at 200° C. None of the blends were extrudable as each bogged down the extruder.

EXAMPLE 8

This example also illustrates the necessity of adding water to lower the Tg of the polymer for processing.

Seventy-five g of AQ38 pellets and 25 g of black iron oxide are ball milled in a one quart mill using 1 inch ceramic balls to yield a free flowing powder with average particle size of 80 mesh. To 50 g of this mixture is added 137.5 g black iron oxide to make an 80:20 blend of iron oxide and AQ38. This blend is ball milled in a one quart container using ½ inch porcelain balls to yield a free flowing powder with an average particle size of 80 mesh.

An aqueous dispersion of the ball milled material is prepared by adding 50 g of material to 50 g of water at 75° C. while stirring. The temperature is held at 75° C. for 30 minutes with stirring. Upon cooling the fineness of dispersion is measured with a grind gage. The average of three measurements is 50 microns.

EXAMPLE 9

This example illustrates that a minimum amount of polymer is required to treat the pigment particles and give the desired properties.

A 95:5 blend of black iron oxide and AQ38 polymer is prepared by blending 475 g iron oxide and 25 g AQ38, which had previously been pulverized to an average particle size of 80 mesh, on a Hobart mixer.

170 g of water is gradually added to the dry blend while mixing to yield a moist blend. The blend is then extruded through a perforated die to yield short cylindrical extrudates. The water content of the extrudate is 25%.

The water is removed from the extrudate by drying overnight in an oven at 50° C. to yield a solid, non-dusty material.

The dried extrudate is dispersed in water as previously described in Example 4. The resulting dispersion has a gritty feel when applied to the skin and the particle size as measured on a grind gage is greater than 50 microns.

EXAMPLE 10

This example illustrates the use of an aqueous dispersion of pigment material obtained by the process described in a mascara formulation. An aqueous dispersion of pigment material as obtained from the process described in Example 3 is prepared at 50% concentration by adding 120 g of pigment material to 120 g of water at 70° C. while mixing with a propeller mixer. The pigment dispersion is added at 50° C. to a W/O emulsion of mascara base using propeller agitation. The concentration of the pigment dispersion in the mascara is 15%. The resulting mascara is smooth and of uniform color.

EXAMPLE 11

This example illustrates the improved flow characteristics of pigment treated by the process of this invention.

A quantity of treated iron oxide pigment and untreated iron oxide pigment are each ground with a hammer mill through a 0.5 mm screen. The angle of repose of each of the pigments is then measured. The untreated iron oxide does not flow and its angle of repose can only be measured by tapping the sides of the funnel repeatedly to force the material to flow out. The angle of repose measured in this fashion is 38.7°. The treated iron oxide pigment flows smoothly from the funnel and its angle of repose is 35°.

EXAMPLE 12

The following figure illustrates the composition of blends of black iron oxide, AQ38 and water suitable for an extrusion process similar to that described in Example 3. In FIG. 1, area A represents the preferred range and area B the broad range.

The minimum amount of polymer useful in this process is 10% of the weight of the dry pigment/polymer blend. Below this amount there is not enough polymer present to coat the surfaces of the pigment particles and the material obtained does not yield a fine dispersion. Mixtures of polymer and water without pigment are processable but not practical. For practical applications, pigment/polymer blends of 50:50 or higher are required. The preferred pigment/polymer weight ratio is 60:40 to 85:15.

The amount of water required is dependent upon the pigment/polymer ratio since the water not only serves to lower the Tg of the polymer but is needed for lubrication as well. As more polymer is used less water is required for lubrication. The minimum amount of water required is that necessary to lower the Tg of the polymer by 20° C. The maximum amount of water is also dependent upon the pigment polymer ratio but should not exceed 50% of the composition. Beyond this amount the mixture is either to liquid for processing or water is squeezed out when it is subjected to shear. The preferred range of water is 20 to 50% of the weight of the pigment/polymer blend.

EXAMPLE 13

This example illustrates the preparation of a water dispersible copolymeric polyester pigment employing the described process.

The copolymeric polyester pigment used is hydrophobic and is not wet by water. Typical particle size of the pigment is:

| % Relative Volume | Particle Size (microns) |
|---|---|
| 10 | 2.13 |
| 50 | 6.99 |
| 90 | 15.40 |

The ingredients used contain the following composition:

| Ingredients | Amount (g) |
|---|---|
| Copolymeric pigment | 225 |
| AQ38 | 96.4 |
| Water | 200 |

The ingredients are mixed, extruded and dried as previously described in Example 9. The result is a pigment blend consisting of short cylindrical segments which can be readily dispersed in water at 65° C. to yield a dispersion of 10% pigment concentration. The particle size distribution of the resulting dispersion is:

| % Relative Volume | Particle Size (microns) |
|---|---|
| 10 | 2.78 |
| 50 | 7.23 |
| 90 | 14.39 |

EXAMPLE 14

This example illustrates the preparation of a non-dusty, water dispersible phthalocyanine blue pigment material (pigment blue 15, MW 575.5) by using the process of this invention.

| Ingredients | Amount (g) |
|---|---|
| Phthalo Blue | 600 |
| AQ55 | 200 |
| Water | 343 |

The ingredients are mixed, extruded and dried as described in Example 9. The extrusion temperature is 65° C. The result is a solid, non-dusty pigment blend which is readily dispersible in water at 75° C. This is in sharp contrast to the untreated pigment which is low density, dusty powder that is very difficult to disperse in water.

EXAMPLE 15

This example illustrates the preparation of a solid, water dispersible mica, bismuth oxychloride and iron oxide treated pigment material using the process of this invention.

The pigment used in this example is a blend of 45% mica, 30% bismuth oxychloride and 25% iron oxide. It is available from Van Dyk under the name Chroma-lite.

| Ingredients | Amount (g) |
| --- | --- |
| Chroma-lite Bronze | 175 |
| AQ38 | 75 |
| Water | 120 |

The ingredients are mixed, extruded and dried as previously described in Example 9. The result in a solid, non-dusty pigment blend which can be easily dispersed in water using the process described in Example 4. The dispersion when applied to the skin has a smooth feel and forms a colored, flexible film upon drying. The untreated Chroma-lite is extremely hydrophobic and is not water dispersible.

EXAMPLE 16

The process described in Example 9 is repeated using the following ingredients:

| Ingredients | Amount (g) |
| --- | --- |
| Titanium Dioxide | 375 |
| AQ38 | 125 |
| Water | 70 |

The result is a solid, non-dusty material which is dispersible in water as described in Example 4. The resulting dispersion, when applied to the skin has a smooth feel and forms a flexible colored film upon drying.

EXAMPLE 17

This example illustrates the differences between pigment/polymer blends processed with and without the presence of water.

An 80:20 blend of iron oxide and AQ38 is prepared by mixing pulverized AQ38 with black iron oxide powder. This blend is divided into two portions.

The first portion is processed by depositing the dry blend onto a two roll mill operating at 175° C. front roll temperature and 150° C. back roll temperature, allowing the material to band, then continuing mixing for about 5 minutes. The pigment/polymer blend is stripped from the mill and allowed to cool to room temperature.

To the second portion of the dry blend is added 34% by weight of water with mixing. This wet blend is processed in a similar manner as the first portion except the front roll temperature is 45° C. and the back roll temperature is 43° C. The pigment/polymer blend is stripped from the mill and placed in an oven at 40° C. overnight to dry.

The appearance of the two blends is quite different. The first blend is shiny black and is quite flexible in that it can be turned back upon itself without breaking. The second blend is dull black in appearance and breaks readily when bent.

Dispersions of both blends are prepared by adding 50 g of material to 50 g of water at 75° C. and mixing for 30 minutes. Each blend results in a fine uniform dispersion of low viscosity. When applied to the skin, and allowed to dry, the dispersion from the first blend forms a soft rubbery film with no adhesion to the skin. The dispersion from the second blend forms a flexible film with good skin adhesion.

EXAMPLE 18

This example demonstrates the ease with which treated pigment blends may be incorporated into a liquid make-up.

The following pigments are blended 80:20 with AQ38 and processed by extrusion as previously described in Example 3:
Titanium dioxide
Talc
Yellow iron oxide
Red iron oxide
Brown iron oxide The treated pigment blends are used in the preparation of a liquid make-up with the following composition:

| | Amount (g) |
| --- | --- |
| Oil Phase | |
| stearic acid | 20.0 |
| propylparaben | 1.0 |
| mineral oil | 100.0 |
| glyceryl monostearate (pure) | 20.0 |
| isopropyl lanolate | 10.0 |
| Powder Phase | |
| titanium dioxide/AQ blend | 70.0 |
| talc/AQ blend | 70.0 |
| yellow iron oxide/AQ blend | 3.6 |
| red iron oxide/AQ blend | 3.6 |
| brown iron oxide/AQ blend | 2.8 |
| Water Phase | |
| water | 655.0 |
| triethanolamine | 10.0 |
| propylene glycol | 30.0 |
| sodium carboxymethylcellulose | 2.5 |

The pigments are dispersed in the water phase at 85° C. prior to the addition of the oil phase. The resulting preparation is smooth, of uniform color, and has a creamy feel when applied to the skin. This preparation is comparable to a similar preparation of the same composition which uses untreated pigments. The untreated pigments are added to the water phase and then passed through a colloid mill prior to the addition of the oil phase.

EXAMPLE 19

A mascara is prepared with the following composition:

| | Amount (g) |
| --- | --- |
| Water Phase | |
| stearic acid | 24.0 |
| glycerol monostearate | 12.0 |
| cetyl alcohol | 32.0 |
| Epolene 14N Wax (Eastman) | 40.0 |
| beeswax | 40.0 |
| paraffin wax 125/130 | 40.0 |
| propylparaben | 0.8 |
| Oil Phase | |
| water | 372.8 |
| triethanolamine | 9.6 |
| Germall 115 (Sutton Labs) | 2.4 |
| methylparaben | 2.4 |
| sodium carboxymethylcellulose | 8.0 |
| Pigment Composition | |
| water | 120.0 |
| black iron oxide/AQ blend | 120.0 |

The pigment/polymer blend is dispersed in water at 70° C. and added to the mascara after the oil and water phases have been combined.

This preparation is compared to another mascara prepared in an identical fashion except with untreated black iron oxide (no polyester present) substituted for the treated pigment material. The mascara prepared with treated pigment is glossier and forms a more uniform film of greater color depth than the mascara prepared with untreated pigment.

EXAMPLE 20

This is a comparative example illustrating that dispersing polymer in water prior to adding pigment will result in a material having a viscosity too low for processing and will not result in a fine dispersion of pigment within the water/polymer blend.

A 40% dispersion of AQ38 in water is prepared by adding polymer to water at 85° C. with vigorous agitation. To 500 g of the polymer dispersion is added 500 g of iron oxide while mixing with a Hobart mixer. The wet blend is extruded through a 3.18 mm perforated die. The extrudate is a viscous liquid which flows together into one mass as it is collected from the extruder. The liquid extrudate is gritty indicating that agglomerates of pigment particles are present. The zero shear-rate viscosity of the extrudate is 70,000 poise as measured with a Rheometrics Stress Rheometer model 8600 at 24° C. with a constant shear stress of 500 dynes/cm$^2$.

To 200 g of pulverized AQ38 is added 300 g water while mixing at room temperature with a Hobart mixer. To the polymer/water blend is added 500 g of iron oxide and mixing is continued for 5 minutes. The wet blend is extruded through a 3.18 mm perforated die. The extrudate is a semisolid malleable material with a zero shear-rate viscosity of 10,000,000 poise as measured as described above with a constant shear stress of 2000 dynes/cm$^2$.

The invention has been described in detail with particular reference to preferred embodiments thereof, but it will be understood that variations and modifications can be effected within the spirit and scope of the invention.

We claim:

1. A pigment composition comprising:
   (A) about 7 to about 48 weight % of a linear, water-dispersible polyester material having an inherent viscosity of at least about 0.1 as measured in a 60/40 parts by weight solution of phenol/tetrachloroethane at 25° C. and at a concentration of 0.5 gram of polyester in 100 ml of solvent, and said polyester material having incorporated therein at least one sulfomonomer,
   (B) about 25 to about 73 weight % of a pigment material, and
   (C) about 5 to about 50 weight % of water, wherein said pigment composition comprises a continuous phase which comprises a major portion of said water and a major portion of said polyester material and a dispersed phase which comprises a major portion of said pigment material, and wherein said polyester material of said pigment composition has an average particle size of less than 1 μm; and wherein said pigment composition has a zero shear rate viscosity of greater than or equal to 500,000 poise.

2. The pigment composition blend of claim 1, wherein component (A) is about 10 to about 33 weight %, component (B) is about 40 to about 71 weight %, and component (C) is about 16 to about 34 weight %.

3. The pigment composition of claim 1 wherein the average size of said polyester material is less than about 1 μm, and wherein the zero shear rate viscosity is greater than or equal to 1,000,000 poise.

4. The pigment composition of claim 1 having water removed such that the composition has a moisture content of less than 20 weight %.

5. The pigment composition of claim 4 in the form of a substantially non-dusty particulate material.

6. The pigment composition of claim 1 wherein said polyester material is one or more linear water-dissipatable polymers having carbonyloxy linking groups in the linear molecular structure wherein up to 80% of the linking groups are carbonylamido linking groups, the polymer having an inherent viscosity of from about 0.1 to about 1.0 measured in a 60/40 parts by weight solution of phenol/tetrachloroethane at 25° C. and at a concentration of 0.25 gram of polymer in 100 mL of the solvent, the polymer containing substantially equimolar proportions of acid equivalents (100 mole % to hydroxy and amino equivalents (100 mole %), the polymer comprising the reaction products of reactants selected from (1), (2), (3), and (4), or the ester forming or esteramide forming derivatives thereof, as follows, wherein all stated mole percentages are based on the total of all acid, hydroxyl and amino equivalents being equal to 200 mole %:

(1) at least one difunctional dicarboxylic acid;
(2) from about 4 to about 25 mole % of at least one difunctional sulfomonomer containing at least one metallic sulfonate group or nitrogen-contained non-metallic sulfonate group attached to an aromatic or cycloaliphatic nucleus wherein the functional groups are hydroxy, carboxyl or amino;
(3) at least one difunctional reactant selected from a glycol or a mixture of a glycol and diamine having two —NRH groups, the glycol containing two —CH$_2$—OH groups of which
   (a) at least 15 mole % is a poly(ethylene glycol) having the structural formula

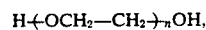

n being an integer of from 2 to about 20, or
   (b) of which from about 0.1 to less than about 15 mole % is a poly(ethylene glycol) having the structural formula

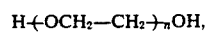

n being an integer of between 2 and about 500, and with the proviso that the mole % of said poly(ethylene glycol) within said range is inversely proportional to the quantity of n within said range;
(4) from none to about 40 mole % of difunctional reactant selected from hydroxycarboxylic acids having one —C(R)$_2$—OH group, aminocarboxylic acids having one —NRH group, and aminoalcohols having one —C(R)$_2$—OH group and one —NRH group, or mixtures of said difunctional reactants; and
wherein each R in the (3) and (4) reactants is a hydrogen atom or an alkyl group of 1 to 4 carbons.

7. The pigment composition of claim 6 wherein said polyester has an inherent viscosity of from about 0.28 to about 0.35, a Tg of about 50 to 60, an acid moiety of from about 75 to about 84 mole % isophthalic acid and conversely from about 25 to about 16 mole % 5-sodiosulfoisophthalic acid, and a glycol moiety of from about 45 to about 60 mole % diethylene glycol and conversely from about 55 to about 44 mole % 1,4-cyclohexanedimethanol or ethylene glycol or mixtures thereof.

8. The pigment composition of claim 7 wherein said acid moiety comprises from about 80 to about 83 mole % isophthalic acid and conversely from about 20 to about 17 mole % 5-sodiosulfoisophthalic acid, and said glycol moiety comprises from about 52 to about 56 mole % diethylene glycol and conversely from about 48 to about 44 mole % 1,4-cyclohexanedimethanol.

9. The pigment composition of claim 6 wherein said polyester material has an inherent viscosity of about 0.38 to 0.44, a Tg of about 27 to 31, an acid moiety of about 87 to 91 mole % isophthalic acid and conversely about 13 to 9 mole % 5-sodiosulfoisophthalic acid, and a glycol moiety of about 98 to 100 mole % diethylene glycol.

10. The pigment composition of claim 6 wherein said polyester material has an inherent viscosity of about 0.34 to 0.38, a Tg of about 36 to 38, an acid moiety of about 87 to 91 mole % isophthalic acid and conversely about 13 to 9 mole % 5-sodiosulfoisophthalic acid, and a glycol moiety of about 76 to 80 mole % diethylene glycol and conversely about 20 to about 24 mole % 1,4-cyclohexandimethanol.

11. A dispersion comprising the pigment composition blend of claim 1 dispersed in a polar solvent system.

12. The dispersion of claim 6 wherein said polar solvent system comprises at least 10 weight % water.

* * * * *